(12) United States Patent
Baschnagel

(10) Patent No.: US 8,833,550 B2
(45) Date of Patent: Sep. 16, 2014

(54) NASAL SPRAY AND TISSUE DISPENSER

(76) Inventor: Robert J. Baschnagel, Garden City, NY (US)

(*) Notice: Subject to any disclaimer, the term of this patent is extended or adjusted under 35 U.S.C. 154(b) by 507 days.

(21) Appl. No.: 12/647,057

(22) Filed: Dec. 24, 2009

(65) Prior Publication Data

US 2011/0155128 A1 Jun. 30, 2011

(51) Int. Cl.
B65D 69/00 (2006.01)
A61M 11/00 (2006.01)
A61M 31/00 (2006.01)
A61M 15/08 (2006.01)

(52) U.S. Cl.
CPC .............. *A61M 31/00* (2013.01); *A61M 11/008* (2014.02); *A61M 2210/0618* (2013.01); *A61M 15/08* (2013.01); *Y10S 206/812* (2013.01)
USPC ............ 206/233; 206/229; 206/812; 222/192

(58) Field of Classification Search
USPC ............ 221/92, 96, 97; 222/192; 128/200.22; 206/216, 518, 229, 233, 812
See application file for complete search history.

(56) References Cited

U.S. PATENT DOCUMENTS

| | | | | |
|---|---|---|---|---|
| 2,789,725 A | * | 4/1957 | Carper | 401/125 |
| 4,946,033 A | * | 8/1990 | Conner | 206/223 |
| 6,321,937 B1 | * | 11/2001 | DeSimone et al. | 221/45 |
| 7,370,754 B2 | * | 5/2008 | Kushner | 206/38 |
| 7,374,039 B2 | * | 5/2008 | Farmer | 206/229 |
| 8,006,864 B2 | * | 8/2011 | Fryan et al. | 221/96 |
| 2003/0143016 A1 | | 7/2003 | Kushner et al. | |
| 2007/0267436 A1 | | 11/2007 | Abbott et al. | |

FOREIGN PATENT DOCUMENTS

JP 59-106881 U 7/1984

OTHER PUBLICATIONS

International Search Report and Written Opinion PCT/US2010/061968 dated Sep. 16, 2011.

* cited by examiner

*Primary Examiner* — Laura Bouchelle
(74) *Attorney, Agent, or Firm* — Scully, Scott, Murphy & Presser, P.C.

(57) ABSTRACT

A spray package including: a container defining a cavity, the cavity having first and second compartments; a spray projection having an orifice in fluid communication with the first compartment; the container having an outlet in communication with the second compartment; a therapeutic liquid disposed in the first compartment and being discharged through the orifice upon application of a force to the container; and one or more tissues disposed in the second compartment, the one or more tissues being removable from the second compartment through the outlet.

11 Claims, 6 Drawing Sheets

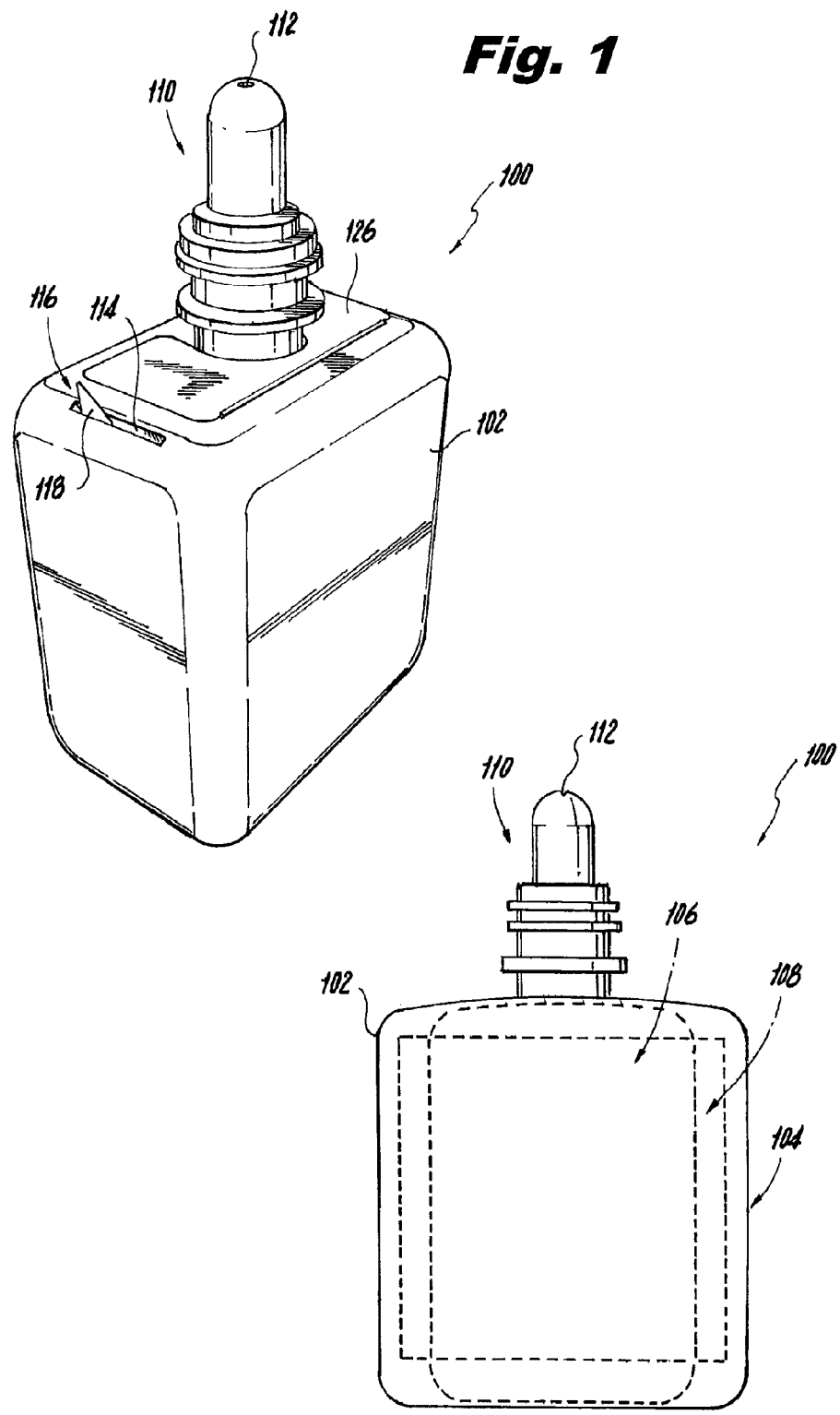

NASAL SPRAY AND TISSUE DISPENSER

BACKGROUND

1. Field

The present invention relates generally to nasal spray packages and, more particularly, to nasal spray packages having a tissue dispenser incorporated therein.

2. Prior Art

Nasal spray packages are well known in the art. Typically, such nasal spray packages are plastic bottles having a therapeutic liquid contained in an interior cavity. Such nasal spray packages further have an orifice in communication with the cavity through which the therapeutic liquid is sprayed when the bottle is squeezed. The therapeutic liquid can be for example, saline, antihistamine or steroid sprays.

SUMMARY

Accordingly, a spray package is provided. The spray package comprising: a container defining a cavity, the cavity having first and second compartments; a spray projection having an orifice in fluid communication with the first compartment; the container having an outlet in communication with the second compartment; a therapeutic liquid disposed in the first compartment and being discharged through the orifice upon application of a force to the container; and one or more tissues disposed in the second compartment, the one or more tissues being removable from the second compartment through the outlet.

The first compartment can be interior to the second compartment. The spray package can further comprise one or more force transfer members disposed between and inner surface of the second compartment and an outer surface of the first compartment to transfer the force from the second compartment to the first compartment.

The outlet can be a slit.

The container can be formed of a first container comprising the first compartment and the projection and a second container comprising the second compartment and the outlet. The first container can be removable from the second container.

The therapeutic liquid can be selected from a group consisting of saline, antihistamine, alcohol, astringent, handwash, eyewash, disinfectant and steroid.

The one or more tissues can be loaded with a therapeutic liquid selected from a group consisting of handwash and astringent Also provided is a liquid and tissue dispenser comprising: a container defining a cavity, the cavity having first and second compartments; a spray projection in fluid communication with the first compartment; a therapeutic liquid disposed in the first compartment; and one or more tissues disposed in the second compartment.

The container can have a first weakened area, which when pulled creates an orifice for dispensing the therapeutic fluid from the first compartment.

The container can have a second weakened area, which when pulled creates an outlet for dispensing the one or more tissues from the second compartment.

The therapeutic liquid can be selected from a group consisting of saline, antihistamine, alcohol, astringent, handwash, eyewash, disinfectant and steroid.

The one or more tissues can be loaded with a therapeutic liquid selected from a group consisting of handwash and astringent.

The projection can be foldable onto an outer surface of the container.

The first compartment can be positioned at a first corner of the container.

The second compartment can be positioned at a second corner of the container.

BRIEF DESCRIPTION OF THE DRAWINGS

These and other features, aspects, and advantages of the apparatus and methods of the present invention will become better understood with regard to the following description, appended claims, and accompanying drawings where:

FIG. 1 illustrates an isometric view of a first embodiment of a spray package.

FIG. 2 illustrates a side view of the spray package of FIG. 1.

DETAILED DESCRIPTION OF THE PREFERRED EMBODIMENT

Figure 3:
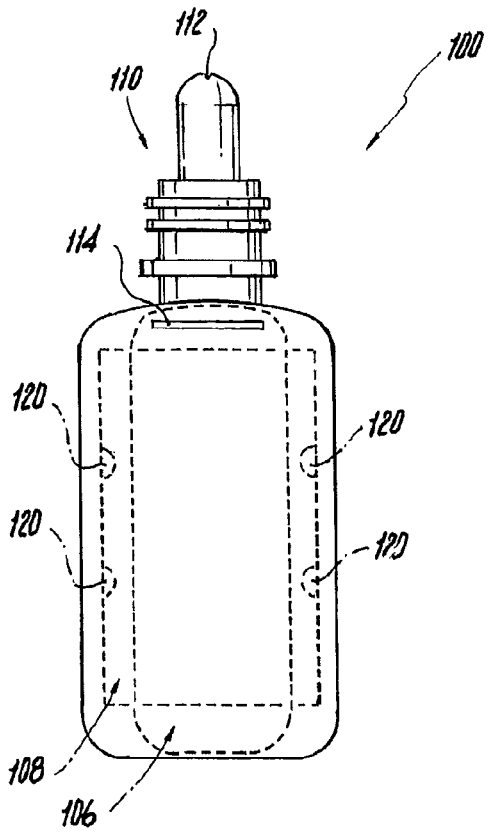
FIG. 3 illustrates an end view of the spray package of FIG. 1.

Referring now to FIGS. 1-3, there is shown a first embodiment of a liquid and tissue dispenser, refereed to generally as a spray package, generally indicated by reference numeral 100. Although such spray package may have particular utility as a nasal spray package, the same is not limited thereto. As discussed below, the spray package 100 can have other uses in medicine, home, cosmetic and industrial uses.

The spray package 100 includes a container 102 defining a cavity 104, where the cavity has at least first 106 and second 108 compartments. The spray package 100 also includes a spray projection 110 having an orifice 112 in fluid communication with the first compartment 106. The first compartment 106 can be interior to the second compartment 108 as shown in FIGS. 2 and 3.

Although not shown, the spray projection 100 can have a cap removable disposed thereon, such as by a female thread mating with a male thread on the spray projection 110 or by any other means known in the art, such as a snap fit. The container 102 further has an outlet 114 in communication with the second compartment 108. The outlet can be configured in any shape, such as a slit.

A therapeutic liquid is disposed in the first compartment 106 and can be discharged through the orifice 112 of the spray projection 110 upon application of a force to the container 102. The type of discharge can be controlled depending upon the size and shape of the orifice 112 and characteristics of the therapeutic liquid, such as viscosity. The therapeutic liquid can be any liquid, such as saline, antihistamine, alcohol, astringent, hand wash, eyewash, disinfectant and steroid.

One or more tissues, wipes, clothes and the like (referred to hereinafter as "tissues" 116) are disposed in the second compartment 108 such that the one or more tissues are removable from the second compartment 108 through the outlet 114. The one or more tissues can also be loaded with a therapeutic liquid selected such as handwash or astringent. A first (or only) of such tissues can be "primed" for removal from the outlet 114 by having a small portion 118 extending from the outlet 114 such that when pulled, the remaining portions of the tissue 116 can be pulled from the outlet 114. Alternatively, a small tab (not shown) may be adhered to the tissue 116 and extending through the outlet 113 such that it can be pulled in the same manner as the portion 118. If more than one tissue 116 is provide, such tissues can be intermingled such that when one is pulled from the outlet, the portion 118 of a subsequent tissue extends from the outlet 114, as is well known in the art of tissue boxes. The tissues 16 can be wrapped around an exterior of the first compartment 106. Such wrapped tissues 116 can facilitate transferring a force applied to the container 102 from the second compartment 108 to the first compartment 106. Alternatively, one or more force transfer members 120 can be disposed between an inner surface of the second compartment 108 and an outer surface of the first compartment 106 to transfer the force applied to the container 102 from the second compartment 108 to the first compartment 106 so that the therapeutic liquid can be discharged from the orifice 112. Such force transfer members, can be one or more bumps or beads formed or adhered on the inner surface of the second compartment 108 or the outer surface of the first compartment 106.

Figure 4:
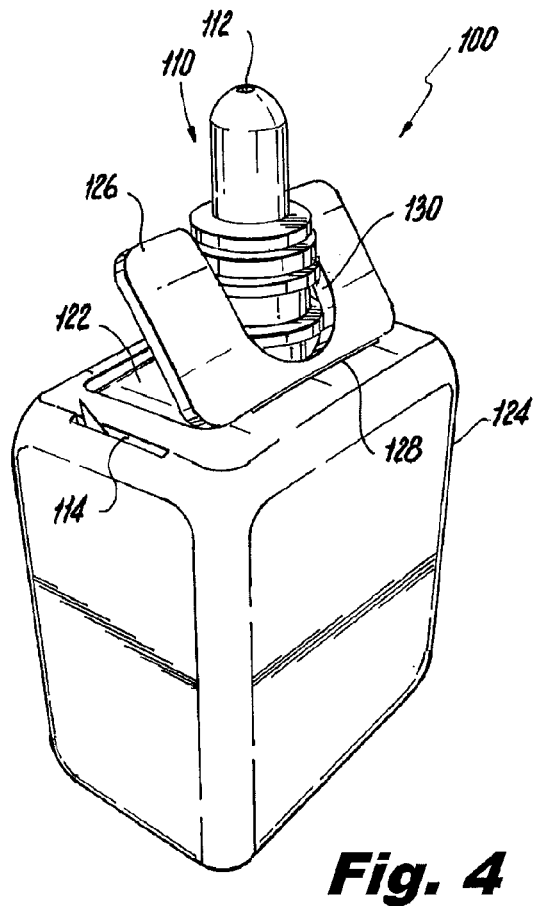
FIG. 4 illustrates an isometric view of the spray package of FIG. 1 in which a compartment is shown being removed.
Figure 5:
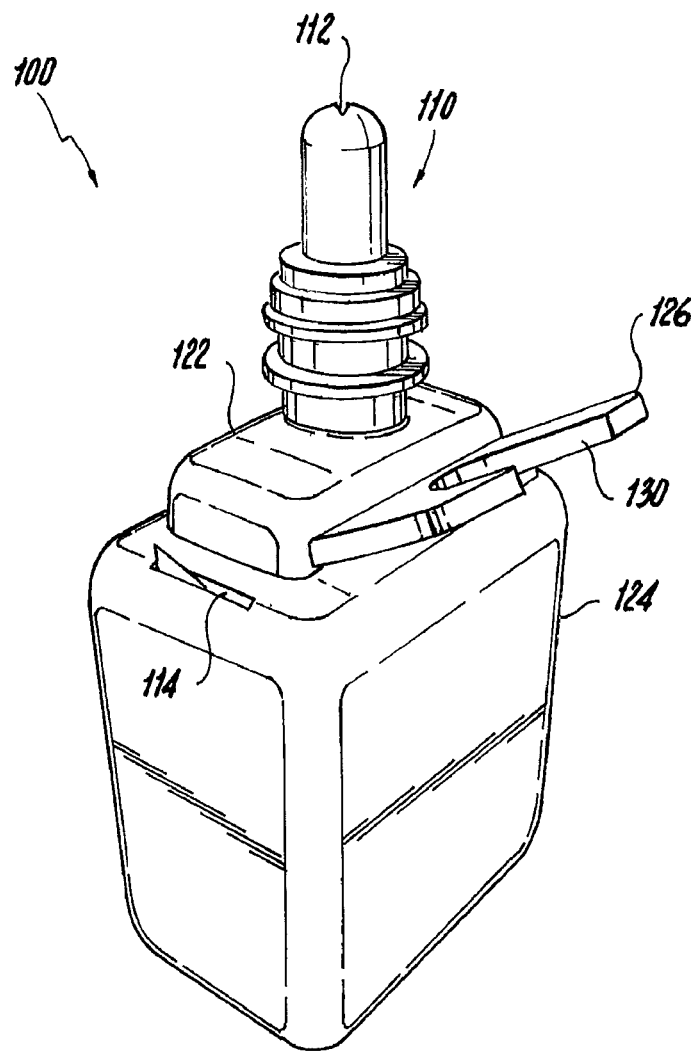
FIG. 5 illustrates an isometric view of the spray package of FIG. 4 in which the compartment is shown being replaced and retained.

Referring now to FIGS. 4 and 5, the container 102 can be formed of a first container 122 comprising the first compartment 106 and the projection 110 and a second container 108 comprising the second compartment 108 and the outlet 114 where the first container 122 is removable from the second container 124. Thus, the second container 124 can be replenished with the tissues 116 after exhaustion thereon or replaced with a new second container already containing a fresh supply of tissues 116. Similarly, the first container 122 can be replaced with a new first container 124 having a fresh supply of therapeutic liquid. Either one of the therapeutic liquid or tissues 116 can be the same as originally used or different.

As shown in FIGS. 4 and 5, the second container 124 can have an access door 126 having a hinge 128 and a cut-out for the spray projection 130. The hinge can be of any known in the art, such as those referred to as "living" hinges. The door 126 can be pried open with a fingernail of the user and can be closed with a snap fit as is known in the art. Once the access door 126 is opened, the first container 122 can be removed therefrom and can be replaced into the same or a different second container 124.

Figure 6:
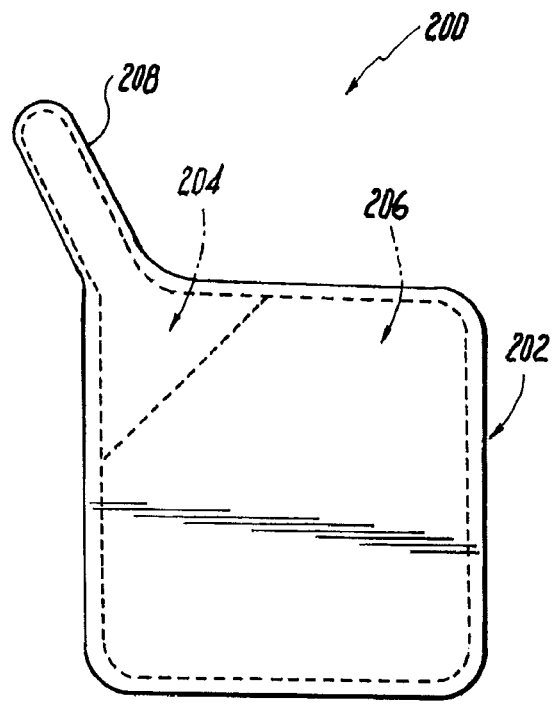
FIG. 6 illustrates a side view of a second embodiment of a spray package.
Figure 7:
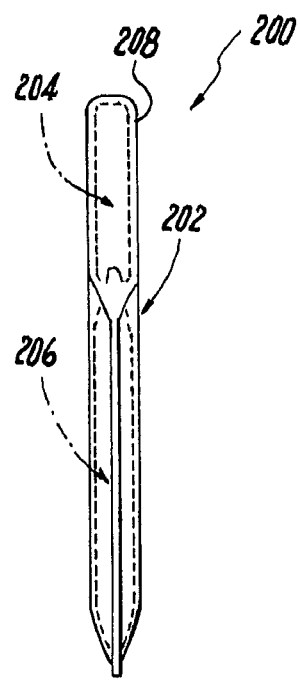
FIG. 7 illustrates an end view of the spray package of FIG. 6.
Figure 8:
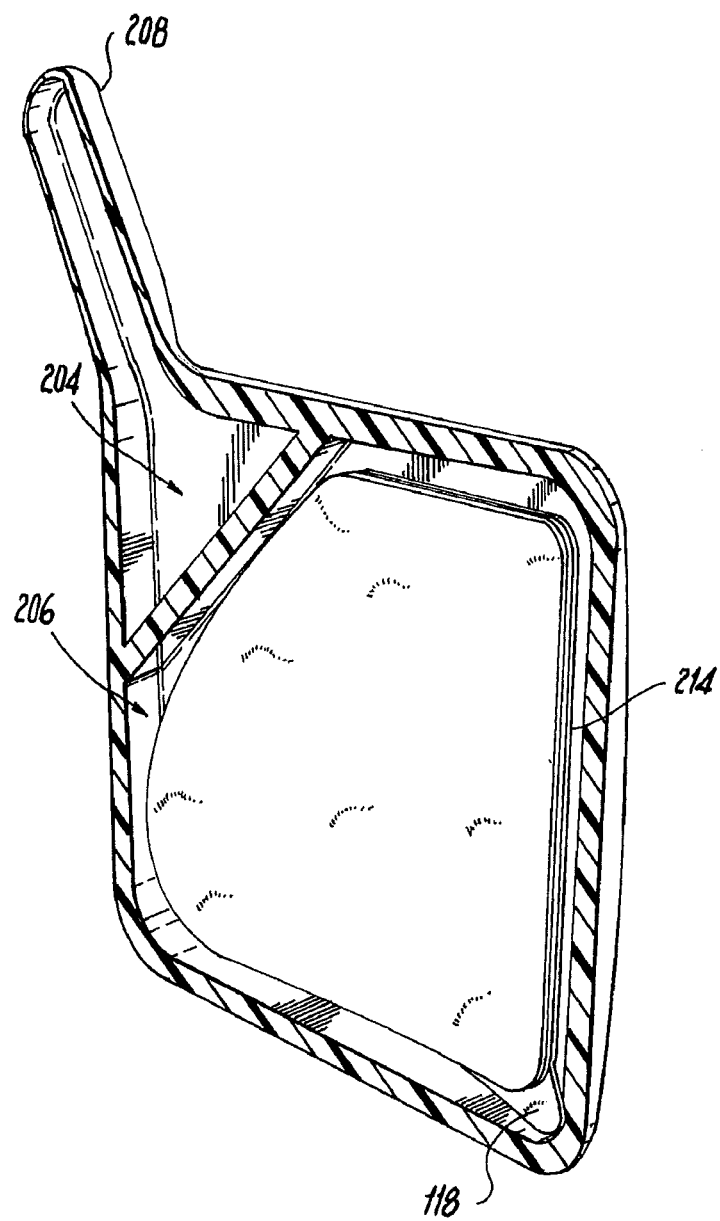
FIG. 8, illustrates a sectional view of the spray package of FIG. 6.

Referring now to FIGS. 6 and 7, there is shown a second embodiment of a liquid and tissue dispenser, generally referred to as a dispenser and generally indicated by reference numeral 200. The dispenser 200 includes a container 202 defining a cavity where, like the first embodiment, the cavity has first 204 and second 206 compartments. A spray projection 208 in fluid communication with the first compartment 204 is provided as well as a therapeutic liquid disposed in the first compartment 204. One or more tissues are disposed in the second compartment 206. Such therapeutic liquid and tissues can be of any type known in the art, such as those discussed above with regard to the first embodiment. The first and second compartments 204, 206 can be disposed such that the first compartment 204 is positioned at a first corner of the container and the second compartment 206 is positioned at a second corner of the container as is clearly illustrated in the cross-section al view of FIG. 8.

Figure 9:
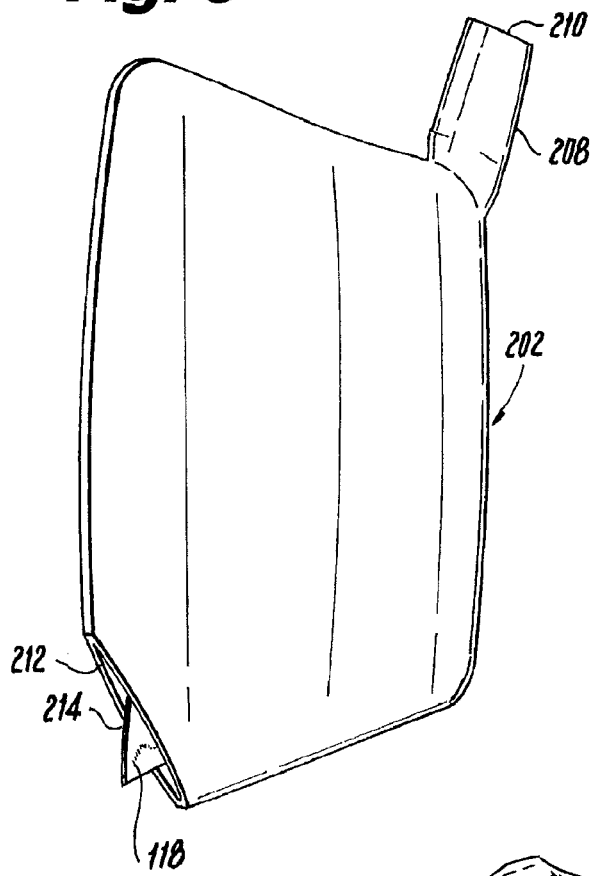
FIG. 9 illustrates an isometric view of the spray package of FIG. 6 in which a corner is removed to access the tissue dispenser.

Referring now to FIG. 9, the dispenser 200 is generally disposable and does not include an orifice for discharging the therapeutic liquid from the projection 208 or an outlet for removal of the tissues. However, the projection and second compartment is formed of a material that is easily torn or has a first weakened area 210, which when pulled creates an orifice for dispensing the therapeutic fluid from the first compartment and a second weakened area 212, which when pulled creates an outlet for dispensing the one or more tissues 214 from the second compartment (which is/are exposed after tearing the second weakened portion 212). The material being easily torn or having a weakened area that is easily torn as generally referred to hereinafter as being a weakened area.

Figure 10:
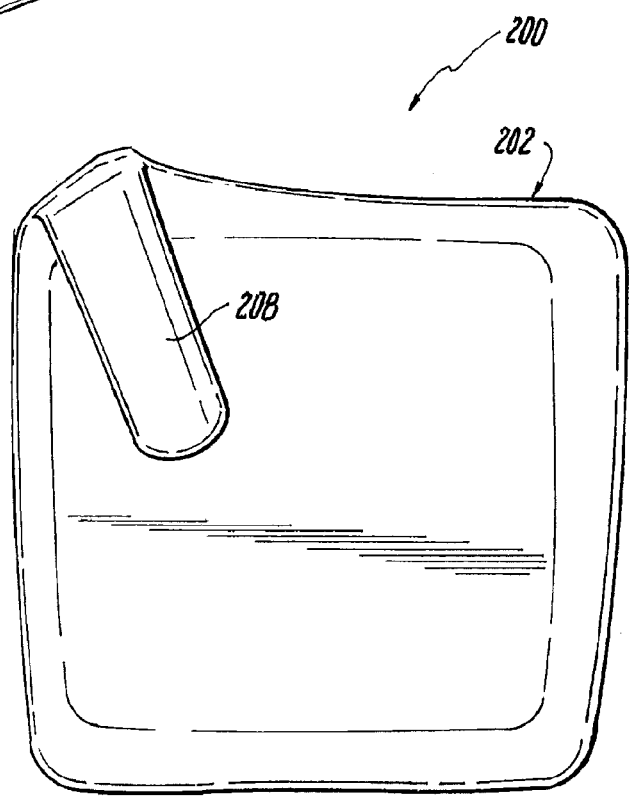
FIG. 10 illustrates the spray package of FIG. 6 in a folded configuration.

Referring now to FIG. 10, the projection 208 can be foldable onto an outer surface of the container 202 so as to be more portable and/or to condense the same for packaging, such as in sterile clear cellophane or other material package.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A spray package comprising:
   a container defining a cavity, the cavity having first and second compartments, the container having a thickness defined by its smallest outer dimension;
   a spray projection having an orifice in fluid communication with the first compartment, the spray projection having a thickness defined by its outer dimension;
   the container having an outlet in communication with the second compartment;
   a therapeutic liquid disposed in the first compartment and being discharged through the orifice upon application of a force to the container; and
   one or more tissues disposed in the second compartment, the one or more tissues being removable from the second compartment through the outlet;
   wherein the thickness of the container is substantially the same as the thickness of the spray projection;
   wherein the container has a weakened area, which when pulled creates the orifice for dispensing the therapeutic fluid from the first compartment.

2. The spray package of claim 1, wherein the outlet is a slit.

3. The spray package of claim 1, wherein the container is formed of a first container comprising the first compartment and the projection and a second container comprising the second compartment and the outlet.

4. The spray package of claim 1, wherein the therapeutic liquid is selected from a group consisting of saline, antihistamine, alcohol, astringent, handwash, eyewash, disinfectant and steroid.

5. The spray package of claim 1, wherein the one or more tissues are loaded with a therapeutic liquid selected from a group consisting of handwash and astringent.

6. A liquid and tissue dispenser comprising:
   a container defining a cavity, the cavity having first and second compartments, the container further having a thickness defined by its smallest outer dimension;
   a spray projection in fluid communication with the first compartment, the spray projection having a thickness defined by its outer dimension;

a therapeutic liquid disposed in the first compartment; and
one or more tissues disposed in the second compartment;
wherein the thickness of the container is substantially the same as the thickness of the spray projection;
wherein the container has a weakened area, which when pulled creates an outlet for dispensing the one or more tissues from the second compartment.

7. The dispenser of claim 6, wherein the therapeutic liquid is selected from a group consisting of saline, antihistamine, alcohol, astringent, handwash, eyewash, disinfectant and steroid.

8. The dispenser of claim 6, wherein the one or more tissues are loaded with a therapeutic liquid selected from a group consisting of handwash and astringent.

9. The dispenser of claim 6, wherein the first compartment is positioned at a first corner of the container.

10. The dispenser of claim 9, wherein the second compartment is positioned at a second corner of the container.

11. A liquid and tissue dispenser comprising:
a container defining a cavity, the cavity having first and second compartments, the container further having a thickness defined by its smallest outer dimension;
a spray projection in fluid communication with the first compartment, the spray projection having a thickness defined by its outer dimension;
a therapeutic liquid disposed in the first compartment; and
one or more tissues disposed in the second compartment;
wherein the thickness of the container is substantially the same as the thickness of the spray projection;
wherein the projection is foldable onto an outer surface of the container.

* * * * *